(12) United States Patent
Li et al.

(10) Patent No.: US 8,877,220 B2
(45) Date of Patent: Nov. 4, 2014

(54) SELF-EXPANDABLE BIOPOLYMER-MINERAL COMPOSITE

(75) Inventors: Shu-Tung Li, Franklin Lakes, NJ (US); Hui-Chen Chen, Franklin Lakes, NJ (US); Debbie Yuen, Franklin Lakes, NJ (US)

(73) Assignee: Collagen Matrix, Inc., Franklin Lakes, NJ (US)

( * ) Notice: Subject to any disclaimer, the term of this patent is extended or adjusted under 35 U.S.C. 154(b) by 89 days.

(21) Appl. No.: 12/850,758

(22) Filed: Aug. 5, 2010

(65) Prior Publication Data
US 2012/0035741 A1  Feb. 9, 2012

(51) Int. Cl.
| *A61F 2/28* | (2006.01) |
| *B29C 35/02* | (2006.01) |
| *B29C 70/06* | (2006.01) |
| *B29C 35/16* | (2006.01) |
| *B29C 70/02* | (2006.01) |

(52) U.S. Cl.
CPC ............... *A61F 2/28* (2013.01); *B29C 70/025* (2013.01); *B29C 35/16* (2013.01); *B29C 35/02* (2013.01)
USPC ........................... 424/422; 623/23.58; 264/28

(58) Field of Classification Search
None
See application file for complete search history.

(56) References Cited

U.S. PATENT DOCUMENTS

| 4,795,467 | A |   | 1/1989  | Piez et al. |             |
|-----------|---|---|---------|-------------|-------------|
| 5,455,231 | A |   | 10/1995 | Constantz et al. |        |
| 5,571,181 | A | * | 11/1996 | Li          | 623/23.75   |
| 5,573,771 | A |   | 11/1996 | Geistlich et al. |        |
| 6,187,047 | B1|   | 2/2001  | Kwan et al. |             |
| 6,300,315 | B1|   | 10/2001 | Liu         |             |
| 7,189,263 | B2|   | 3/2007  | Erbe et al. |             |
| 7,241,316 | B2|   | 7/2007  | Evans et al.|             |
| 7,381,224 | B1| * | 6/2008  | Li et al.   | 623/23.51   |
| 7,544,212 | B2|   | 6/2009  | Li et al.   |             |
| 2003/0232071 | A1| * | 12/2003 | Gower et al. | 424/443  |
| 2004/0138758 | A1| * | 7/2004  | Evans et al. | 623/23.51 |
| 2009/0043400 | A1|   | 2/2009  | Evans et al. |          |
| 2009/0112317 | A1| * | 4/2009  | Li et al.    | 623/16.11 |
| 2009/0246244 | A1| * | 10/2009 | McKay et al. | 424/423  |

FOREIGN PATENT DOCUMENTS

| CA | 2713761 A | 8/2009 |
| EP | 0197693   | 10/1986 |
| EP | 0243178   | 10/1987 |

OTHER PUBLICATIONS

*International Search Report*, PCT Application No. PCT/US2011/045748, mailed Mar. 20, 2012 (7 pages).

* cited by examiner

*Primary Examiner* — Robert A Wax
*Assistant Examiner* — Danah Al-Awadi
(74) *Attorney, Agent, or Firm* — Cesari and McKenna, LLP

(57) ABSTRACT

A compressed implant composite for repairing mineralized tissue. The compressed implant composite includes a matrix formed of biopolymeric fibers and a plurality of calcium- and/or silicate-based mineral particles dispersed in the matrix. The matrix constitutes 4 to 80% by weight and the mineral particles constitute 20 to 96% by weight of the composite. The composite is free of soluble collagen and is expandable to a volume 2 to 100 times of its compressed volume (e.g., upon absorption of water). Also disclosed are methods of preparing the above-described composite.

24 Claims, 2 Drawing Sheets

|  | Compact form | Expanded form |
|---|---|---|
| Figure 1a: cylindrical geometry |  |  |
| Figure 1b: conical geometry |  |  |
| Figure 1c: spherical geometry |  |  |
| Figure 1d: bullet shaped geometry |  |  |
| Figure 1e: wedge shaped geometry | 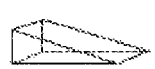 | 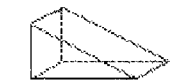 |

SELF-EXPANDABLE BIOPOLYMER-MINERAL COMPOSITE

BACKGROUND

When mineralized tissue (e.g., bone) is damaged as a result of injury or disease, it is often necessary to provide an implant or graft to facilitate healing or preventing further damage. Natural or synthetic bone graft materials (such as hydroxyapatite) have been used in mineralized tissue repair (such as orthopedic or dental surgery). See, e.g., U.S. Pat. Nos. 6,846,853 and 7,381,224. There is a continuing need for improved bone graft materials. To securely affix the materials to target sites, flexibility, compression modulus and directional self-expandable properties are important considerations.

SUMMARY

This invention relates to a self-expandable implant composite for repairing mineralized tissue such as bone, and teeth.

In one aspect, the present invention features a compressed implant composite including a matrix formed of biopolymeric fibers and a plurality of calcium- and/or silicate-based mineral or ceramic particles dispersed in the matrix. As used in this application, the terms "mineral" and "ceramic" are interchangeable and each refer to a mineral and/or a ceramic. The matrix constitutes 4 to 80% (e.g., 10-50% or 15-30%) by weight and the mineral particles constitute 20 to 96% (e.g., 50-90% or 70-85%) by weight of the composite. The composite is free of soluble collagen and is self-expandable to a volume 2 to 100 times (e.g., 5 to 50 times) of its compressed volume. The self-expansion is triggered upon absorption of water or aqueous fluid (e.g., body fluid such as blood). The composite upon hydration can have a pore size of 25-500 μm (e.g., 50-400 μm or 75-250 μm), and a density range of 0.05-0.8 g/cm$^3$ (e.g., 0.1-0.6 g/cm$^3$). The composite can also have a compression modulus ranging from 2 to 30 N/cm$^2$ in the dry compressed state (e.g., 6N/cm$^2$) and ranging from 1 to 15 N/cm$^2$ (e.g., 2N/cm$^2$) in the hydrated expanded state.

The biopolymeric fibers used for preparing the matrix can be natural polymers, such as polypeptide fibers (e.g., collagen, elastin, or fibrin), polysaccharide fibers (e.g., cellulose, alginic acid, chitosan), or a combination thereof. In one embodiment, the biopolymeric fibers are insoluble collagen fibers (including native insoluble collagen and reconstituted insoluble collagen fibers). The biopolymeric fibers can be cross-linked.

The term "soluble collagen" refers to soluble individual tropocollagen molecules in acidic aqueous environments. Tropocollagen may be considered the monomeric unit of collagen fibers and its triple helix structure is well recognized. The term "native insoluble collagen" as used herein refers to a polymeric collagen network (such as collagen fibril and fibers) formed in vivo via intrinsic intermolecular crosslinks, which cannot be solubilized in an aqueous solution absent chemical or enzymatic modification. The insoluble collagen includes but not limited to collagen fibrils and fibers from tendon, ligament, skin, or bone of mammals. For example, it can be derived from the corium, which is the collagen-rich layer of an animal hide that is situated between the epidermis and the subcutaneous fat.

The calcium- or silicate-based mineral particles, such as various natural or synthetic calcium phosphates, calcium sulfate, calcium-phosphate based apatite (e.g., carbonate apatite), and silicate-based glass ceramics (e.g., 45S5 bioglass) can have a particle size of 1-5000 microns or 0.001 to 5 mm (e.g., 100-1500 microns). More detail about calcium- and silicate-based minerals and ceramics can be found in LeGeros, Raquel Z., Calcium Phosphate Materials in Restorative Dentistry: A Review. *Adv. Dent. Res.,* 1988, 2(1): 164-180; U.S. Pat. No. 5,977,204, and U.S. Pat. No. 5,728,753.

In another aspect, the present invention features a method of preparing a self-expandable implant composite. The method includes dispersing biopolymeric (e.g., collagen) fibers in an aqueous solution (preferably basic) to form a suspension or dispersion, homogenizing the suspension using a homogenizer, such as a Silverson homogenizer (Longmeadow, Mass.), to form a uniform fiber dispersion, mixing the fiber homogenized dispersion with a plurality of calcium- and/or silicate-based mineral particles to form a fiber-mineral mixture, freeze-drying the mixture to obtain a dried fiber-mineral mixture, cross-linking the dried mixture, and compressing the crosslinked mixture to form a fiber-mineral composite. The composite is free of soluble collagen. The method may include hydrating the cross-linked mixture before the compressing step and then refreeze drying the compressed hydrated mixture to form a fiber-mineral composite. The advantage of a second freeze-drying step is that the composite matrix maintains its compressed configuration in the dry state and self-expands only when it is in contact with an aqueous fluid. Thus, the delivery of this refreeze-dried implant composite can easily be accomplished by simply inserting the implant with forceps or other small hand holding tools without the use of a tubular delivery device. The method can also include sterilizing and packaging the compressed composite in a delivery device.

Further, this invention relates to a method for repairing mineralized tissue having a defect site. The method includes delivering a compressed implant composite of the invention to the defect site so as to allow the compressed implant composite to self expands when in contact with fluid of the body (e.g., extracellular fluid or blood) and fill the defect site.

The compressed implant composite of the present invention has one or more of the following advantages. The composite can be delivered with or without a cannula (e.g., an open barrel syringe) to the target bone defect site so that it self-expands to the dimension of the void resulting in a porous scaffold to support bone growth and facilitate healing. The self-expansion is triggered by absorption of body fluid (e.g., blood; bone marrow) at the defect site. Additional liquid (sterile water or saline) may be added to the implant composite to facilitate the self expansion. As the composite is flexible and self-expandable, it can readily conform to the geometry of the defect and affix itself to the defect even when the defect has an irregular geometry.

The details of one or more embodiments of the invention are set forth in the description below. Other features, objects, and advantages of the invention will be apparent from the drawings, description, and from the claims.

BRIEF DESCRIPTION OF THE DRAWINGS

FIGS. 1a-1e are perspective views of a few embodiments of the self-expandable composite implant in both compressed and expanded configurations: a. cylindrical; b. conical; c. spherical; d. bullet-shaped; and e. wedge-shaped geometries.

DETAILED DESCRIPTION

Figure 2:
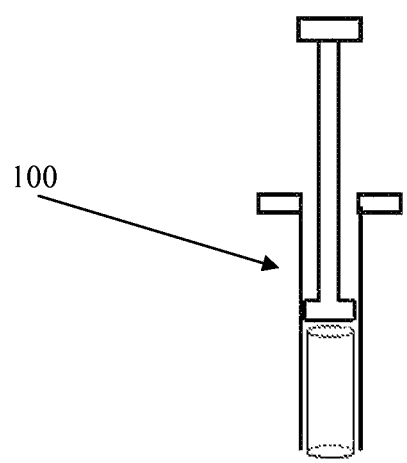
FIG. 2 is a cross-sectional view of a device for delivering the self-expandable composite implant of cylindrical geometry in its compressed configuration.

As described above, the biopolymeric matrix in the implant composite of this invention can be polypeptide (e.g., collagen) matrix.

The collagen matrix preferably prepared from type I, type II or type III collagen fibers. In particular, type I collagen fibers from humans, animals, or from genetically engineered methods are most preferred. Native insoluble type I collagen fibers can be isolated and purified from type I collagen-rich tissues such as skin, tendon, ligament, and bone of humans and animals. The methods of isolation and purification of collagen fibers have been described in E. J. Miller, Methods in Enzymology, vol. 82, pp. 33-64, 1982; The Preparation of Highly Purified Insoluble Collagen, Oneson, I., et al., Am. Leather Chemists Assoc., Vol. LXV, pp. 440-450, 1970; and in U.S. Pat. No. 6,090,996. Genetically engineered collagen fibers such as those marketed by Fibrogen (South San Francisco, Calif.) can also be used for this invention. As well known in the art, dispersed collagen fibers, at or near their isoelectric point, reconstitute and aggregate into longer fibers, which completely separate from the solution phase. This process is called coacervation. Depending on how they are prepared, different collagen fibers have different isoelectric points. In the bone implant composite of this invention, the collagen matrix can be made of either coacervated or native insoluble collagen fibers.

The biopolymeric fibers can also be polysaccharides. Polysaccharides that can be used for the implant composite include but are not limited to chitin-based materials (e.g., chitosan) obtained from shell fish, plant and bacteria-based cellulose, seaweed-based alginic acid, and animal or human-based glycosaminoglycans (e.g., hyaluronic acid). Various polysaccharides for implant manufacturing are available commercially (e.g., Sigma).

The calcium- or silicate-based mineral particles dispersed in the biopolymeric matrix preferably have a particle size of 0.1-3.0 mm and more preferably of 0.1-1.5 mm. The mineral can be a synthetic or naturally occurring calcium-containing substance or silicate-based bioactive glass that is suitable for medicinal use. Examples include, but are not limited to various calcium phosphate compounds, calcium sulfate, calcium carbonate, anorganic bone mineral (a natural carbonate apatite), synthetic carbonate apatite, 4555 bioglass and hydroxyapatite. Natural or synthetic carbonate apatite is apatite that contains carbonate ions, generally in the ranges from 2 to 12%. See, e.g., *Journal of Materials Science Materials in Medicine*, 1998, 9 (12): 779-83. The carbonate content of the carbonate apatite preferably ranges from 2 to 8% (e.g., 3-7%). In one embodiment, the compressed implant composite has a 20:80 weight ratio of collagen to mineral and has a density of 0.1-0.6 g/cm$^3$ upon expansion.

The bone implant composite of this invention can be prepared by the following steps: (1) dispersing and homogenizing the above described collagen fibers in an aqueous solution to form a homogeneous dispersion, (2) mixing calcium- and/or silicate-based mineral particles with the dispersion to form a mixture, (3) freeze-drying the mixture, (4) contacting the dried mixture with a crosslinking agent to crosslink the collagen fibers and form a composite with the crosslinked collagen, and (5) compressing the crosslinked composite. These steps each are described in detail below.

(1) Dispersing

A type I collagen fiber dispersion can be prepared by the following procedure. Collagen fibers (1% to 2% by weight) are first swollen in 0.01-0.05M NaOH solution. The swollen collagen fibers are then homogenized using a commercially available homogenizer (e.g., Silverson Homogenizer) to obtain a uniform dispersion of collagen fibers.

(2) Mixing

Carbonate apatite particles (0.1-1.5 mm in size), obtained from Collagen Matrix, Inc. (Franklin Lakes, N.J.), are slowly added to the collagen fiber dispersion. The ratio of weight percent of collagen to mineral is predetermined to define the final composition of the composite. The collagen fibers and mineral particles are then gently stirred to uniformly mix the collagen fibers and mineral particles.

(3) Freeze-Drying

The just-described collagen-mineral mixture is then poured into molds of a defined volume and geometry followed by a freeze-drying step using a commercial freeze dryer (e.g., Virtis). As an example, a 250 ml of the collagen-mineral mixture is frozen at −40° C. and dried at −20° C. for about 24 to 48 hours and finally at 20° C. for about 8-24 hours under vacuum at about 100 millitorr. After frozen water is removed, the spaces that it occupied become pores. As a result, a dried collagen-mineral mixture having a porous collagen matrix and mineral particles dispersed therein is formed. One can prepare a bone implant having a desired pore size and, in turn, a desired density by controlling the amount of water prior to the freeze-drying process. For example, one can partially remove water from the mixture in order to afford a bone implant having a small pore size and a high density. The water may be removed and density controlled by centrifuging the mixture at various speed.

(4) Cross-Linking

The freeze-dried collagen-mineral mixture thus obtained is then subjected to a cross-linking reaction, in which the collagen fibers are covalently bonded to each other via a suitable cross-linking agent (e.g., an aldehyde compound). The dried mixture can be brought in contact with a vapor generated from a solution containing a cross-linking agent, the extent of cross-linking being controlled by the vapor pressure, the solution temperature, and the reaction time. Methods for determining the extent of cross-linking are well known in the art, e.g., by monitoring the hydrothermal transition temperature or by determining the number of intermolecular cross-linking points. See Yuen, et al., *Trans. Soc. Biomaterials*, 1288, 2000 and Wiederhorn, et al., *J. Polymer Sci.*, 9:315, 1952. The composite containing the crosslinked collagen matrix defines the maximum size of the implant in vivo.

(5) Compressing

The crosslinked collagen-mineral composite is then subjected to a compression procedure that decreases the size of the collagen matrix of the composite. For example, if the crosslinked composite is a 10 mm diameter cylinder, the compression can reduce the diameter of the cylinder to between 1-5 mm depending on the initial density of the mixture. See, e.g., FIG. 1*a*. Further, if the crosslinked cylinder composite has a height of 10 mm and the compression is in the direction along the longitudinal direction, the height of the cylinder can be reduced to 1-5 mm. Thus, by applying the directional compression, a predetermined size and shape of the compressed cylindrical composite can be formed. Similarly, any other size and shape of the matrix can be reduced to a predetermined size and shape by an appropriate compression procedure. See, e.g., FIGS. 1*b*-1*e*. The compressed matrix can then be loaded into a delivery device of matched size. For example, when the compressed composite is a cylinder, the matrix is loaded into a tubular delivery vehicle (e.g., an open barrel syringe 100 as shown in FIG. 2). The syringe can be inserted into a defect and release the implant at the defect site. In one embodiment, the crosslinked composite is moisturized in a humidifying chamber for about 1 to 6 hours to absorb 10 to 40% by weight of moisture. The moisturized matrix has a softer texture and when compressed maintains a more cohesive geometry for easy insertion into a tubular delivery device. Depending on the specific surgical application, the internal diameter (ID) of the delivery device varies.

As an example, when the composite implant is used as a bone grafting matrix for tooth socket preservation, the ID of the delivery device is generally in the range of from about 3 mm to about 6 mm.

Alternatively, the compressed implant can be delivered directly using forceps if the compression step is followed by a second freeze drying step similar to that described above. More specifically, the crosslinked composite is hydrated and compressed into a mold that has a predetermined size and shape before it is freeze-dried for a second time. The thus prepared compressed composite can maintain its shape and size when stored in a relatively dry environment. As soon as the implant composite is delivered in vivo and is in contact with the body fluid (e.g., blood, bone marrow) it self expands instantaneously to conform to the defect which preferably has a size smaller than the maximum size the implant composite can expand to. The osmotic pressure within the implant forces it to expand to the walls of the defect and provides a porous structure for cell ingrowth and new tissue deposition (e.g., osteoblast ingrowth and new bone deposition).

The above-described implant composite can be used in orthopedic tissue repair. For example, it can be used in filling bone voids or gaps of the skeletal system, e.g., extremities, spine, and pelvis. It can be provided as a sterile, dry material to be hydrated with autogenous bone marrow at the point of use.

The collagen-mineral composite of this invention may contain one or more growth factors, such as bone morphogenetic proteins (BMPs), platelet derived growth factors (PDGFs), transforming growth factors (TGFs), and bone marrows. It may also include other bioactive agents such as anti-microbial agents. The bioactive agents can be attached to the collagen-mineral matrix via mechanical interactions, electrostatic interactions or covalent bonding. Alternatively, they can be incorporated into a collagen-mineral matrix via physical interactions or diffusion mechanism.

Further, the collagen-mineral composite may contain cells, such as osteoblasts, fibroblasts, stem cells, chondrocytes, sertoli cells, and blood and marrow-based cells. To introduce cells into the collagen-mineral matrix, one can seed cells on the top of the matrix and allow cells to infiltrate into the pores of the matrix. Alternatively, one can directly inject the cells into the pores via a needle. The cells incorporated in the matrix may be allowed to culture in vitro prior to in vivo implantation.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

Example 1.4 g of type I collagen fibers and 0.7 g of anorganic bone mineral (particle size of 100-350 μm) were uniformly mixed in a 200 ml beaker. The collagen fibers were prepared essentially in the same manner as that disclosed in U.S. Pat. No. 6,716,225. The anorganic bone mineral, derived from bovine femur bone by removing organic substances, was a commercial product, i.e., NuOss™ (ACE Surgical Supply, Inc.).

To the above mixture was slowly added 100 ml of 0.01 M NaOH solution. After several hours of agitation, the mixture was homogenized with a Silverson homogenizer for 1 minute, de-aired under vacuum. Additional 5 g of anorganic bone mineral (particle size of 0.25-1000 μm) was added into the homogenized mixture with a mixer and slightly de-aired, and then poured into a mold of defined volume and geometry and freeze dried. The freeze dried collagen anorganic bone composite was crosslinked with formaldehyde vapor generated from 1% formaldehyde solution for 3 hours at ambient temperature to obtain a final crosslinked collagen-mineral composite.

The mineral content, pore size, density, and compression modulus of the collagen-mineral composite were measured by the methods described below:

1. Mineral Content:

The mineral content of a collagen-mineral composite was determined by Ash test. The ash test was conducted by pre-weighing collagen-mineral composite in a crucible and furnaced at 550° C. for 2 hours. Upon completion of the test, the residual ash content was weighed as the mineral content of the composite.

2. Pore Size:

The pore size was measured using scanning electron micrographs. Briefly, a collagen-mineral composite sample was cut in the cross-section and fixed. A micrograph was taken at a certain magnification (e.g., ×50). The pore size was determined as the longest distances of pores.

3. Density:

A collagen-mineral composite sample was first dried under vacuum or over $P_2O_5$ for 24 hours. Its weight was recorded. Its volume was calculated from its dimensions (i.e., the length, width, and thickness), which were measured using a caliper. The density was determined as weight/volume in unit of $g/cm^3$.

4. Compression Modulus:

The compression modulus of the collagen-mineral composite was measured using a Chatillon TCD200 mechanical tester equipped with a compression platform test stand that includes a pair of compression plates. The measurement was conducted as follows: A 1 cm×1 cm sample of the collagen-mineral composite, dry or hydrated (immersed in water for 5 minutes), was placed between the compression plates. The sample was compressed at a rate of 1.25 cm/min to the half height of its original thickness. The peak compression modulus ($kg/cm^2$) was measured and calculated.

The collagen-mineral composite prepared in this example had a 20:80 weight ratio of collagen to anorganic bone mineral, a pore size of 40-300 μm, a density of 0.12 $g/cm^3$, and a compression modulus of about 0.6 $kg/cm^2$ in the dry compressed state and of about 0.2 $kg/cm^2$ in the hydrated expanded state.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A compressed implant composite for repairing mineralized tissue, the composite comprising:
   a cross-linked matrix formed of biopolymeric fibers, and a plurality of calcium- or silicate-based mineral particles dispersed in the matrix, wherein the matrix constitutes 4 to 80% by weight, the mineral particles constitute 20 to 96% by weight, and the composite is free of soluble collagen and is self-expandable to a volume 2 to 100 times of its compressed volume.

2. The composite of claim 1, wherein the composite is expandable upon absorption of water.

3. The composite of claim 1, wherein the composite is expandable upon absorption of body fluid.

4. The composite of claim 1, wherein the composite is expandable to a volume 5 to 50 times of its compressed volume.

5. The composite of claim 1, wherein the biopolymeric fibers are polypeptide fibers, polysaccharide fibers, or a combination thereof.

6. The composite of claim 5, wherein the biopolymeric fibers are insoluble collagen fibers.

7. The composite of claim 1, wherein the calcium-based mineral particles are calcium phosphate or calcium apatite.

8. The composite of claim 7, wherein the calcium apatite is carbonate based apatite.

9. The composite of claim 1, wherein the silicate-based mineral particles are silicate-based bioactive glass.

10. The composite of claim 9, wherein the silicate-based bioactive glass is selected from the group consisting of 45S5 bioglass, 55SF bioglass, and S53P4 bioglass.

11. The composite of claim 1, wherein the calcium- or silicate-based mineral particles have a particle size ranging from 0.001 mm to 5 mm.

12. The composite of claim 11, wherein the calcium- or silicate-based mineral particles have a particle size ranging from 0.1 mm to 1.5 mm.

13. The composite of claim 1, wherein the composite upon self-expansion has a density from 0.05 $g/cm^3$ to 0.8 $g/cm^3$.

14. The composite of claim 13, wherein the composite upon self-expansion has a density from 0.1 $g/cm^3$ to 0.6 $g/cm^3$.

15. The composite of claim 1, wherein the composite upon self-expansion has a pore size from 25 to 500 microns.

16. A method of preparing a bone implant composite of claim 1, the method comprising: dispersing biopolymeric fibers in an aqueous solution, to form a suspension, the biopolymeric fibers being free of soluble collagen; homogenizing the suspension; mixing the homogenized suspension with a plurality of calcium-or-silicate-based mineral particles to form a mixture; freeze-drying the mixture; crosslinking the freeze-dried mixture to form a crosslinked composite; and compressing the crosslinked composite.

17. The method of claim 16, further comprising, after the crosslinking step and before the compressing step, hydrating the crosslinked composite.

18. The method of claim 17, further comprising, after the compressing step, freeze-drying the compressed composite.

19. The method of claim 16, wherein the biopolymeric fibers are polypeptide fibers, polysaccharide fibers, or a combination thereof.

20. The method of claim 19, wherein the biopolymeric fibers are insoluble collagen fibers.

21. The method of claim 16, wherein the calcium-based mineral particles are calcium phosphate or calcium apatite.

22. The method of claim 21, wherein the calcium apatite is carbonate based apatite.

23. The method of claim 16, wherein the silicate-based mineral particles are silicate-based bioactive glass.

24. The method of claim 23, wherein the silicate-based bioactive glass is 45S5 bioglass.

* * * * *